United States Patent [19]
McMichael

[11] Patent Number: 5,576,289
[45] Date of Patent: Nov. 19, 1996

[54] METHODS FOR TREATING MOTOR DEFICITS

[75] Inventor: John McMichael, Delanson, N.Y.

[73] Assignee: Milkhaus Laboratory, Delanson, N.Y.

[21] Appl. No.: 421,231

[22] Filed: Apr. 13, 1995

[51] Int. Cl.$^6$ .................................................. A61K 38/00
[52] U.S. Cl. .................................................. 514/2; 514/23
[58] Field of Search .......................................... 514/2, 23

[56] References Cited

U.S. PATENT DOCUMENTS 5,378,620  1/1995  Adam et al. ............................. 435/183

*Primary Examiner*—Elli Peselev
*Attorney, Agent, or Firm*—Marshall, O'Toole, Gerstein, Murray & Borun

[57] ABSTRACT

Methods are presented for treatment of motor deficit symptoms in patients who have a disease, such as multiple sclerosis, characterized by the presence of motor deficit symptoms.

4 Claims, No Drawings

METHODS FOR TREATING MOTOR DEFICITS

FIELD OF THE INVENTION

The present application relates to methods for treating diseases states characterized by motor deficits.

BACKGROUND OF THE INVENTION

Streptolysin O is one of a group of filterable hemolysins derived from Group A beta-hemolytic streptococci. Specifically, streptolysin O is a 60 kD peptide which is hemolytic in its reduced state but is inactivated upon oxidation. Streptolysin O is used in the art generally as an analytical reagent for permeabilizing cells. See, e.g., Razin, et al., *Proc. Nat'l. Acad. Sci (U.S.A.)*, 91:7722–7726 (1994). In fact, the present Applicant is unaware of any report of a use of Streptolysin O in a therapeutic context.

It has been reported that prior infection with a Group A beta-hemolytic streptococcus is linked to subsequent development of movement disorders. Taranta, et al., *Am. J. Med.*, 20: 170–175 (1956). Moreover, there are reports that patients having Group A beta-hemolytic streptococcal infections produce antibodies against their own neural tissue and that such antibodies are stimulated by the streptococcal infection. Kiessling, et al., *Pediatrics*, 92:39–43 (1993). Interestingly, patients with central nervous system deficits which result in impaired movement have high anti-streptolysin O antibody titers and those antibodies cross-react with myelin basic protein, a suspected causative agent in multiple sclerosis.

Of interest to the present invention are numerous central or peripheral nervous system disorders characterized by movement deficits. Those diseases include multiple sclerosis, autism, Tourette's Syndrome, chorea, and others. Patients who have one of the above-named diseases and whose symptoms include impaired movement generally also have high anti-streptolysin O titers and a history of Group A beta-hemolytic streptococcal infection.

The present invention provides methods for treating patients with a disease state including impaired movement.

SUMMARY OF THE INVENTION

The present invention provides methods for treating disease states in which a motor deficit is a symptom. Methods of the invention result in alleviation or palliation of motor deficits, including loss of movement of limbs, loss of speech ability, loss of control over bowel and/or bladder, spasms, and other similar deficits. Methods of the invention comprise the step of administering an effective amount of streptolysin O to a patient having a disease characterized by motor deficit symptoms. The precise dose will vary among patients. However, preferred doses generally range from about 0.0032 units to about 50 units. A preferred route of administration of streptolysin O is a sublingual route. However, intravenous, intramuscular, subcutaneous, and intrathecal routes of administration are also believed to be effective. If administered sublingually, it is preferred that streptolysin be administered 1–10 drops per day.

Treatment methods according to the invention are effective against any disease in which a motor deficit is a symptom and such diseases include, but are not limited to, multiple sclerosis, autism, Tourette's syndrome, and various forms of chorea. Additional aspects and advantages of the invention will become apparent upon consideration of the following detailed description thereof.

DETAILED DESCRIPTION OF THE INVENTION

It has surprisingly been found that treatment of patients having diseases with a central nervous system component involving a motor system deficit show improvement in symptoms with treatment comprising administration of streptolysin O (Sigma, St. Louis). A motor system deficit is defined herein as an impairment or decrease in the ability of a patient to move normally. This includes impaired speech ability, impaired control over bowel and bladder functions, numbness, loss of coordination, inappropriate movements or speech patterns, as well as loss of control of fine and gross motor functions, including balance. A number of human clinical trials have been conducted and the results are presented herein in the form of several Examples. In each case, clinical histories of the patients were known or taken prior to treatment and evaluations of the patient's condition was conducted periodically during the course of treatment. In many cases, it is standard practice in the medical art to rely on patient reports of symptoms in order to diagnose, treat, and monitor various disease states. The rationale for using a patient's own evaluation of symptoms in certain cases is that for diseases such as multiple sclerosis, autism, Tourette's Syndrome, and many others characterized by a central or peripheral nervous system deficit, there are no reliable laboratory tests, i.e. blood tests, urinalysis, and others, which may be used to monitor symptoms. For multiple sclerosis, for example, the presence of high titers of myelin basic protein is a predictor of the onset and presence of the disease, but there are no reliable indicators to monitor most movement disorders associated with that disease. Accordingly, physician routinely rely on patient reports and observations by attending clinicians to determine whether a course of treatment is having any effect on the motor-deficit component of a disease.

In the present application, patients presenting with a number of diseases having symptoms characterized by a motor deficit were treated using relatively low doses of streptolysin O. In no case was treatment with streptolysin O unsuccessful in alleviating or decreasing motor deficit symptoms in treated patients. A preferred route of administration is sublingually and patients were generally instructed to self-administer from one to about 4 drops daily. Each drop usually contained from about 0.016 units to about 10 units of streptolysin O. The precise does for each patient was determined by the degree of sensitivity displayed in a modified test for allergy to Streptolysin O. Thirty-one patients were initially tested to determine the extent of any allergic response which might be observed by application of small amounts of streptolysin O by either intradermal, sublingual, intravenous, or other suitable means. Testing doses ranged from an initial concentration of 0.0032 Units to a maximum of 50 Units. Proper dosing of a composition according to the present invention may easily be determined by the skilled artisan using standard procedures and upon evaluation of the severity of a patient's symptoms. Streptolysin O for use in methods according to the invention may be formulated in an appropriate vehicle, including water, saline, dextrose, and albumin.

The following Examples are intended to illustrate practice of the preferred embodiments of the invention. Numerous additional embodiments and improvements are apparent upon consideration of the following Examples.

EXAMPLE I

A 44-year-old woman who had been diagnosed with multiple sclerosis at age 38 presented for treatment. Her symptoms included loss of coordination, balance, and mobility. Additionally, the patient suffered from slurred speech, numbness in the limbs, muscle weakness, fatigue, and visual problems. The patient was first treated with hospitalization and 80 mg prednisone daily, along with physical therapy. She was then treated with calcium-EAP three times per week for over one year. Some limited improvement in symptoms was observed upon such treatment, but the patient still suffered from chronic motor deficits as described above.

Treatment with streptolysin O was begun with the patient receiving one drop at a concentration of 10 Units/drop of streptolysin O sublingually per day. After 7 days of treatment, clinicians noted a 50% improvement in motor deficits associated with multiple sclerosis, including improvements in ambulation, speech, and balance. In a follow-up evaluation, attending clinicians recorded additional improvements in motor-deficit symptoms associated with multiple sclerosis. Improvements included an approximately 70% reduction in fatigue as reported by the patient; muscle strength improved 40%; the patient no longer suffered from loss of balance or coordination, the tingling sensation reported by the patient in her limbs was less frequent; numbness in the limbs improved; and the patient's ability to speak improved. In addition, the patient reported that previously-reported difficulty/urgency in urination disappeared after approximately five weeks of therapy. Finally, prior to treatment, the patient reported occasional mood swings, which completely disappeared after five weeks of treatment. During therapy with streptolysin, the patient did not require, and was not administered, any other therapy.

EXAMPLE II

A 68-year-old male patient with a history of multiple sclerosis presented for treatment. For over ten years, the patient had been non-ambulatory and incapable of feeding or bathing himself. Numerous traditional therapies were administered to the patient, without success. Prior to treatment with streptolysin O, the patient was completely unable to move his right arm and the range of motion in his left arm was severely limited.

Streptolysin O therapy was commenced with a dose of 10 Units of streptolysin O administered sublingually once per day. The patient was immediately upon administration of streptolysin O able to move his right arm and the mobility in his left arm was significantly improved over its pretreatment status. In a follow-up visit clinicians noted improved mobility, marked improvement in speech (i.e. less slurring of speech and ability to form words where none was apparent prior to treatment), and increased energy level. After the Mar. 3, 1995 clinical evaluation, streptolysin O therapy was increased to two drops daily at the same dose.

At a second follow-up evaluation it was noted that the patient had full mobility in both arms and could perform tasks such as holding a newspaper. Moreover, the patient indicated that feeling had returned to his legs. He still reported spasms in his lower extremities but he reported that they were less frequent since beginning streptolysin O therapy. A neurocognitive evaluation was conducted and clinicians noted significant improvements in speech ability and a reduction in symptoms of depression which were present prior to treatment. Other than maintaining levels of nutrients via intravenous infusion (due to the inability to eat), no other treatments were administered during streptolysin O therapy.

EXAMPLE III

A 55-years-old man who had been diagnosed with multiple sclerosis presented for treatment. Upon initial evaluation, the patient was non-ambulatory. He had been on immunotherapy for several years without improvement. His symptoms, especially motor deficit symptoms, continued to worsen during that period. The patient's symptoms included erratic bowel movements, numbness, tingling of hands and feet, muscle weakness, tremors, and spasms.

Streptolysin O therapy was begun, with 2 Units of streptolysin O being administered once per day in the form of a single sublingual drop. A follow-up evaluation was conducted after 3 weeks of streptolysin O therapy. During that evaluation, the patient reported a greater range of movement and increased energy and muscle strength. Streptolysin O therapy is continuing.

EXAMPLE IV

A female patient presented with symptoms, including motor deficits, of multiple sclerosis which had been present for several years. Streptolysin O therapy was begun upon initial clinical evaluation. The patient was administered one drop of 10 units of Streptolysin O once per day sublingually. After one week, a follow-up clinical evaluation was conducted, wherein the patient reported a reduction in severity of motor deficits which had been associated with multiple sclerosis. Specifically, the patient reported reduced muscle weakness and an increased range of movement since commencement of streptolysin O therapy. Moreover, the patient reported that she was able to ride a stationary bicycle which she was unable to do prior to streptolysin O therapy.

EXAMPLE V

A 60-year-old male presented with severe multiple sclerosis. The patient was unable to sit in a wheelchair due to head flopping and the inability to maintain an erect posture in the chair. He was unable to move any limb, with the exception of slight movement in one hand. Streptolysin O therapy was begun at a dose of 10 Units. Upon clinical evaluation subsequent to beginning streptolysin O therapy, the patient was able to move both arms in full range, was able to sit in a wheelchair, and no longer experienced head drooping.

The patient was then sent home and instructed to continue streptolysin O therapy. However, the patient broke the dropper of streptolysin O given to him by his physician and thus discontinued therapy. One day later, the patient presented himself to his physicians and his motor function was again severely compromised and all of the previously-observed benefits of increased movement were no longer present. The patient was then given a new dropper containing streptolysin O and again commenced therapy at the same dose as before. One day later, the patient presented for follow-up evaluation after having taken streptolysin O. His condition was again markedly improved, with a full range of motion and the ability to sit. Therapy is continuing with streptolysin O.

EXAMPLE VI

A 20-year-old patient with severe autism presented for treatment. The patient had been administered traditional therapies for several years without success. His symptoms included lack of communication with others. Streptolysin O therapy commenced using one drop at 2 units/drop once daily. Upon post-treatment evaluation, attending clinicians noted a significant improvement in the ability to communicate, including a marked increase in interaction with other pupils in the student's class. Streptolysin O therapy is continuing.

The invention has been presented in the form of its preferred embodiments which are not intended as a limitation.

I claim:

1. A method for treating motor deficit symptoms of a disease state characterized by a motor deficit selected from the group consisting of multiple sclerosis and Tourette's Syndrome, comprising the step of:

administering an effective amount of streptolysin O in a pharmaceutically-acceptable vehicle to a patient having a disease characterized by a motor deficit.

2. The method according to claim 1, wherein said streptolysin O is administered to said patient sublingually in a dose from about 0.0032 units to about 50 units.

3. The method according to claim 1, wherein said streptolysin O is administered by a method selected from the group consisting of intramuscular, sublingual, intravenous, and subcutaneous.

4. The method according to claim 1, wherein said streptolysin O is administered intravenously.

* * * * *